(12) United States Patent
Helms

(10) Patent No.: US 8,697,956 B1
(45) Date of Patent: Apr. 15, 2014

(54) OAT CULTIVAR ROMAR-07

(76) Inventor: Ronnie Sloan Helms, Stuttgart, AR (US)

( * ) Notice: Subject to any disclaimer, the term of this patent is extended or adjusted under 35 U.S.C. 154(b) by 9 days.

(21) Appl. No.: 13/372,070

(22) Filed: Feb. 13, 2012

(51) Int. Cl.
*A01H 5/00* (2006.01)
*A01H 5/10* (2006.01)

(52) U.S. Cl.
USPC .......................................... 800/320; 800/260

(58) Field of Classification Search
None
See application file for complete search history.

*Primary Examiner* — Russell Kallis
(74) *Attorney, Agent, or Firm* — Smith Hurst PLC; Meredith K. Lowry

(57) ABSTRACT

A novel oat cultivar, designated ROMAR-07, is disclosed. The invention relates to the seeds of oat cultivar ROMAR-07, to the plants of oat ROMAR-07 and to methods for producing a oat plant produced by crossing the cultivar ROMAR-07 with itself or another oat variety. The invention further relates to hybrid oat seeds and plants produced by crossing the cultivar ROMAR-07 with another oat cultivar.

8 Claims, No Drawings

OAT CULTIVAR ROMAR-07

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

The present invention relates to a new and distinctive oat cultivar, designated Romar-07 The term "oat" is applied to various grassy crops whose seeds are harvested for human food or animal feed.

Oats are a cool-season cereal grain that are highly preferred by deer. During the first months of growth, typical oat varieties are high in protein (14% to 18% protein) and easily digestible. In most cases, deer prefer oats over the other cereal grains. Oats are most often used in fall-planted hunting plots to attract deer.

Oats include ten to fifteen species in genera *Avena*. Oats are native to Europe, Asia and northwest Africa. All oats have edible seeds, though they are small and hard to harvest in most species. The most important cultivated species of oats are common oat (*Avena sativa*), Abyssinian oat (*Avena abyssinica*), naked or hulless oats (*Avena nuda*), and lopsided oat (*Avena strigosa*).

The present invention relates to *Avena sativa*, commonly known as common oat. *Avena sativa* has many varietal types, including variety type *Avena sativa* var. Bob which is recognized as having a higher yield than either parent, heavier test weight, better crown rust resistance, shorter plant height, higher protein yield, and intermediate winter hardiness.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics on grain quality.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Various recurrent selection techniques were used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, overall value of the advanced breeding lines, and number of successful cultivars produced per unit of input.

Promising advanced breeding lines are tested and compared to appropriate standards in environments representative of the target area. The best lines are candidates for new commercial cultivars; those still deficient in a few traits may be used as parents to produce new populations for further selection.

Development of new cultivars is a time-consuming process that requires precise forward planning, efficient use of resources, and a minimum of changes in direction.

One method of identifying a superior plant is to observe its performance relative to other cultivars. If a single observation is inconclusive, replicated observations provide a better estimate of its genetic worth.

The goal of plant breeding is to develop new, unique and superior oat cultivars and hybrids. The breeder initially selects and crosses two or more parental lines, followed by self-pollination and selection, producing many new genetic combinations. The breeder has no direct control at the cellular level; therefore, two breeders will not develop the same line, or even very similar lines, having the exact same traits.

The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new oat cultivars.

Pedigree breeding is used commonly for the improvement of self-pollinating crops. Two parents which possess favorable, complementary traits are crossed to produce an F1. An F2 population is produced by selfing one or several F1's. Selection of the best individuals may begin in the F2 population; then, beginning in the F3, the best individuals in the best families are selected. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

In a multiple-seed procedure, oat breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

SUMMARY OF THE INVENTION

The present invention is a novel oat cultivar designated Romar-07 with shorter plant height and higher yield potential than other cultivars and it can re-seed itself the following year. This invention thus relates to the seeds of oat cultivar Romar-07, to the plants of oat cultivar Romar-07 and to methods for producing an oat plant by crossing of the cultivar Romar-07 with itself or with another oat line.

The invention further relates to seeds of cultivar Romar-07 further comprising one or more specific, single gene traits. The invention also relates to plants of cultivar Romar-07 further comprising one or more specific, single gene traits. The invention includes methods for producing an oat plant by crossing the oat plant of cultivar Romar-07 further comprising one or more specific, single gene traits with itself or with another oat genotype.

Further, both first and second parent oat plants may be from the oat cultivar Romar-07. Therefore, any methods using the oat cultivar Romar-07 are part of this invention: selfing, backcrosses, hybrid breeding and crosses to populations. All plants produced using oat cultivar Romar-07 as a parent are within the scope of the invention.

DEFINITIONS

In the description and tables that follow, a number of terms are used. In order to provide a clear and consistent understanding of the specification and claims, including the scope to be given such terms, the following definitions are provided:

Maturity Date. Plants are considered mature when 95% of the pods have reached their mature color.

Plant Height. Plant height is taken from the top of soil to top of node of the plant and is measured in centimeters.

Grain Yield. Grain yield is measured in pounds per acre of harvested seed.

Grain Length (L). Length of a oat grain is measured in millimeters.

100 Grain Wt. The weight of 100 oat grains as measured in grams.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

DETAILED DESCRIPTION OF THE INVENTION

Oat cultivar Romar-07 is a high yielding, shorter plant height oat variety that was evaluated from 2007-2010.

The cultivar has shown uniformity and stability, as described in the following variety description information. It has been self-pollinated a sufficient number of generations with careful attention to uniformity of plant type. The line has been increased with continued observation for uniformity.

Oat Cultivar Romar-07 has the following morphologic and other characteristics (based primarily on data collected at Stuttgart, Ark. in comparison to Bob Oats. Plant height is 5% to 10% shorter. The shorter plant height is desirable for foraging oats for wildlife and livestock. Yield potential is 5% to 10% higher. Protein content is higher at 21.8% compared to 18.7% for Bob Oats.

Culture for expressing desired structural genes and cultured cells are known in the art. Likewise, the creation of variants by mutagenesis or transformation of cultivars. Mutation breeding is another method of introducing new traits into cultivars. Mutations that occur spontaneously or are artificially induced can be useful sources of variability for a plant breeder. The goal of artificial mutagenesis is to increase the rate of mutation for a desired characteristic. Once a desired trait is observed through mutagenesis the trait may then be incorporated into existing germplasm by traditional breeding techniques. Details of mutation breeding can be found in "Principles of Cultivar Development" Fehr, 1993 Macmillan Publishing Company.

Mutagenesis of oat can be induced by treatment with a variety of mutagenic agents known in the art, including physical mutagens such as X-rays, gamma rays, fast or thermal neutrons, protons, and chemical mutagens such as ethyl methanesulfonate (EMS), diethyl sulfate (DES), ethyleneimine (EI), propane sultone, N-methyl-N-nitrosourethane (MNU), N-nitroso-N-methylurea (NMU), N-ethyl-N-nitrosourea (ENU) and sodium azide.

As used herein, the term "plant" includes plant cells, plant protoplasts, plant cells of tissue culture from which oat plants can be regenerated, plant calli, plant clumps, and plant cells that are intact in plants or parts of plants, such as pollen, flowers, embryos, ovules, seeds, pods, leaves, stems, anthers and the like. Thus, another aspect of this invention is to provide for cells which upon growth and differentiation produce a cultivar having essentially all of the physiological and morphological characteristics of Romar-07.

Oat Cultivar Romar-07 was obtained from ethyl methanesulfonate (EMS) treatment of the parent strain Bob Oats. In the fall, Bob Oat seeds were soaked in 2.5 L distilled water in a 6 L flask for 9 hours at room temperature. The flask was aerated for the 9 hours of soaking. The water was drained from the flask, and 2.5 L of 0.1 molar phosphate buffer at pH 7 and 0.025 molar EMS were added. The seeds were soaked for 9 hours, the solution was drained and the seeds were rinsed twice with distilled water. Treated seeds were planted 2.5 cm deep in moist soil within 4 hours after the last rinse. The soil was watered regularly to keep it moist until seedling emergence.

In the spring, plant height differences in the first generation of oats, known as M-0, were observed. At this time, plants having a noticeably shorter plant height were selected from the M-0 generation. These selected plants were bulked and used to grow the next generation, M-1. M-1 was planted in the following fall. Again, in the spring, the M-1 generation was observed, selected for lower plant height, and the selected plants were bulked for seed for the next generation, M-2. M-2 was planted in the following fall. In the spring, the M-2 generation was observed, selected for lower plant height, and the selected plants were bulked for seed for the next generation, M-3.

M-3 was planted in the following fall. In the spring, the M-3 generation was observed, selected for lower plant height, and the selected plants were bulked for seed for the next generation, M-4. The M-4 generation was planted the following fall and final selections of plants were made in the spring to purify the cultivar based on plant height.

DEPOSIT INFORMATION

Applicant made a deposit on Jan. 22, 2014 of at least 2500 seeds of the cultivar of the present invention in conformity with requirements with the American Type Culture Collection (ATCC), 10801 University Boulevard, Manassas, Va., 20110-2209 U.S.A., ATCC Accession Number No. PTA-120867. This deposit of cultivar Romar-07 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicant imposes no restrictions on the availability of the deposited material from the ATCC following issuance of the patent; however, Applicants have no authority to waive any restrictions imposed by law on the transfer of biological material or its transportation in commerce.

What is claimed is:

1. A oat seed of the cultivar designated ROMAR-07, wherein a representative sample of said seed has been deposited under ATCC Accession No. PTA-120867.

2. A oat plant, or a part thereof, of cultivar ROMAR-07, wherein a representative sample of seed of said cultivar has been deposited under ATCC Accession No. PTA-120867.

3. Pollen of the plant of claim 2.

4. An ovule of the plant of claim 2.

5. A oat plant, or a part thereof, having all of the physiological and morphological characteristics of the oat plant of claim 2.

6. A seed of the plant according to claim 2, wherein the seed is produced by crossing the plant with itself.

7. A method for producing a oat seed comprising crossing a first parent oat plant with a second parent oat plant and harvesting the resultant hybrid oat seed, wherein said first or second parent oat plant is cultivar ROMAR-07, a representative sample of seed of said cultivar deposited under ATCC Accession No. PTA-120867.

8. A seed of the plant according to claim 5, wherein the seed is produced by crossing the plant with itself.

* * * * *